United States Patent [19]

Hoogeboom

[11] Patent Number: 5,752,972
[45] Date of Patent: May 19, 1998

[54] MODULAR ENDOSCOPIC SURGICAL INSTRUMENT

[76] Inventor: Thomas J. Hoogeboom, 7544 Oak Shore South, Portage, Mich. 49002-7850

[21] Appl. No.: 745,796

[22] Filed: Nov. 8, 1996

Related U.S. Application Data

[60] Provisional application No. 60/006,602, Nov. 9, 1995.

[51] Int. Cl.⁶ .................................................. A61B 17/00
[52] U.S. Cl. ........................................ 606/205; 606/174
[58] Field of Search ................................. 606/1, 51, 52, 606/170, 174, 205–210; 128/750–755

[56] References Cited

U.S. PATENT DOCUMENTS

| | | |
|---|---|---|
| 3,868,957 | 3/1975 | Doddington . |
| 4,760,848 | 8/1988 | Hasson . |
| 4,944,741 | 7/1990 | Hasson . |
| 5,282,817 | 2/1994 | Hoogebeem et al. ........ 606/174 |
| 5,498,256 | 3/1996 | Furnish . |

FOREIGN PATENT DOCUMENTS

| | | |
|---|---|---|
| 0310582 | 9/1988 | European Pat. Off. . |
| 0587413 | 8/1993 | European Pat. Off. . |

*Primary Examiner*—Michael Buiz
*Assistant Examiner*—William Lewis
*Attorney, Agent, or Firm*—Price, Heneveld, Cooper, Dewitt & Litton

[57] ABSTRACT

A modular surgical instrument includes a handle, an end effector, and an elongate tubular sleeve extending between and opposing the end effector and the handle, a reciprocating actuator rod disposed within the sleeve, the end effector being operably connected to a distal end of the actuator rod and having opposed members, at least one of which is movable with respect to another upon sliding movement of the actuator rod within the sleeve, and a handle including a pair of opposing actuating members, the handle having a first end connected to a proximal end of the tubular sleeve, and a second end releasably snap connected to a proximal end of the actuator rod. Compression of the actuating members toward each other causes the actuator rod to move at least one of the opposing members of the end effector with respect to the other. The disclosed arrangement allows an end effector to be easily removed from the handle and replaced with a different end effector, thus reducing costs associated with replacing worn end effectors and eliminating the need for providing each end effector with its own handle.

11 Claims, 6 Drawing Sheets

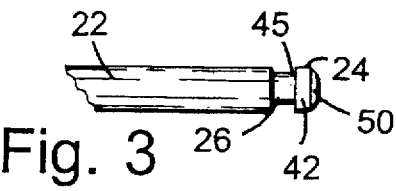
Fig. 3
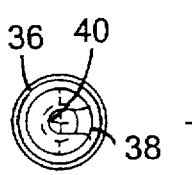
Fig. 8
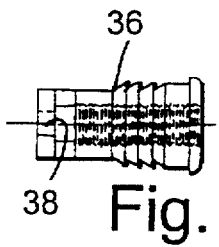
Fig. 6
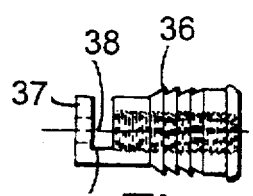
Fig. 7
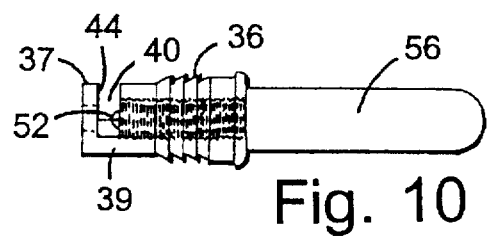
Fig. 10
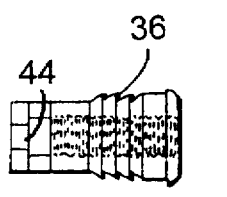
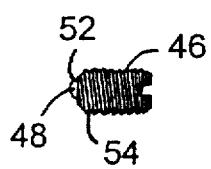
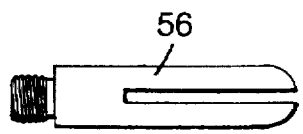
Fig. 9

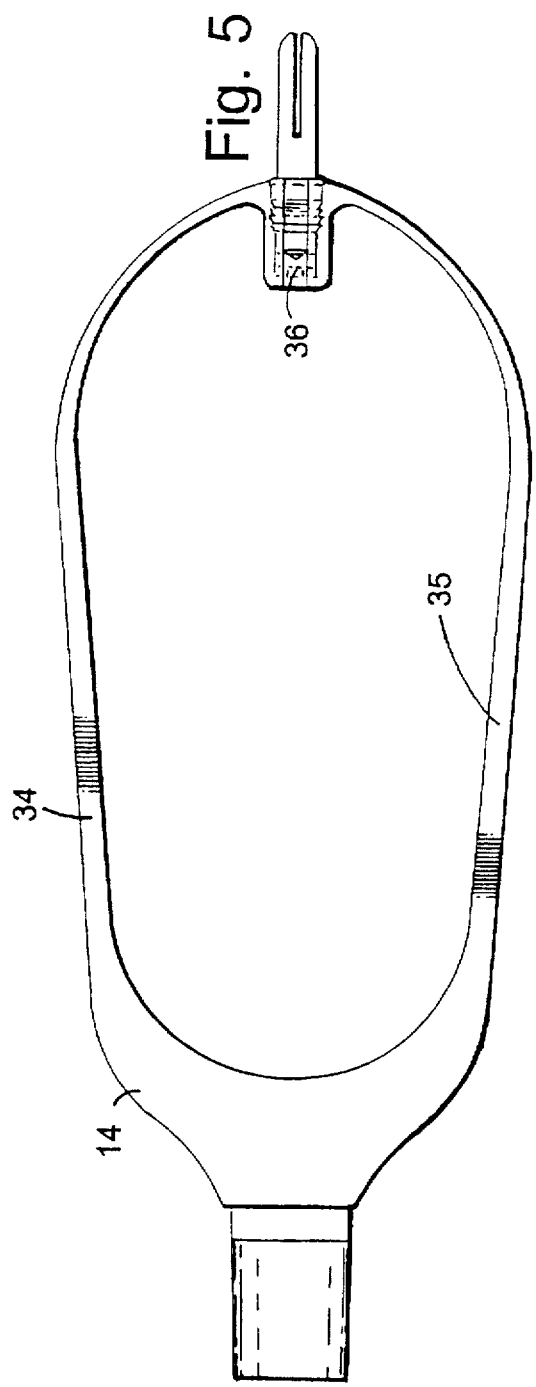
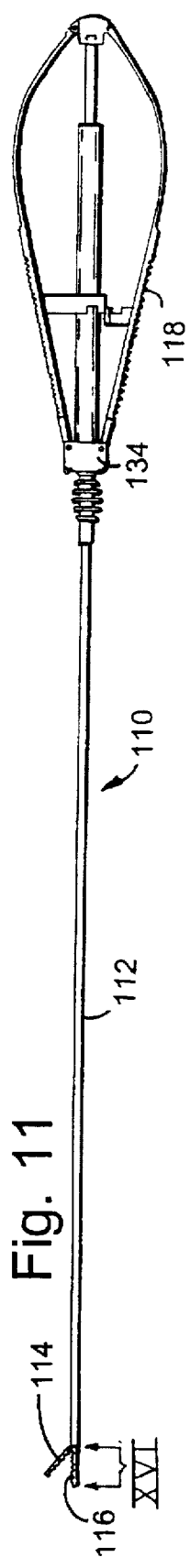
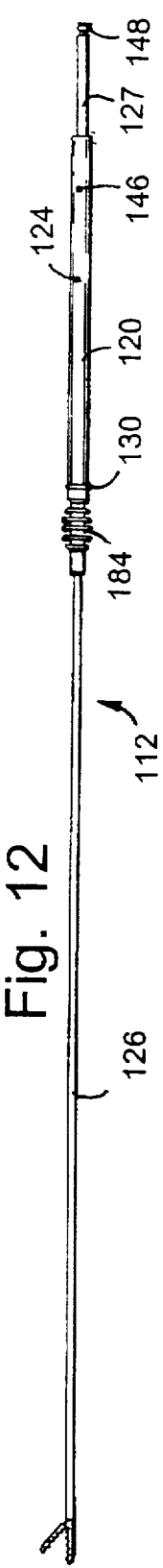

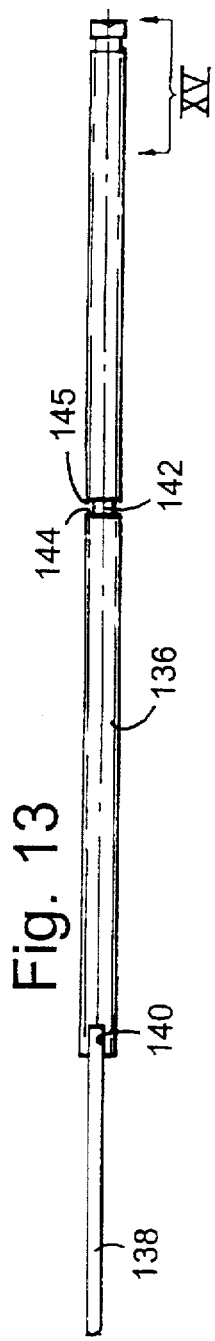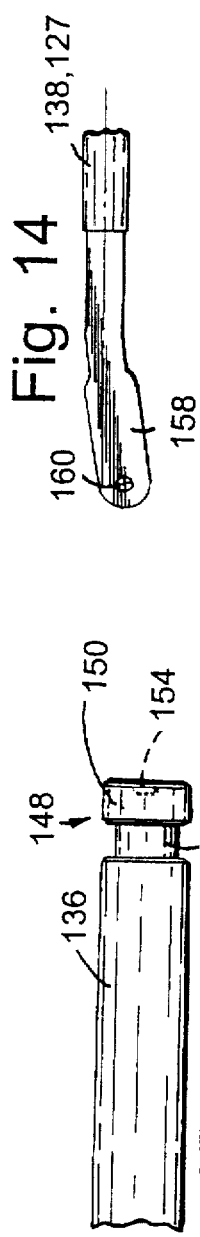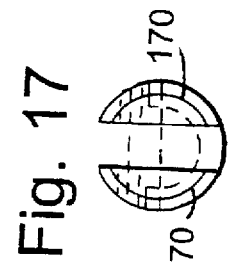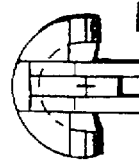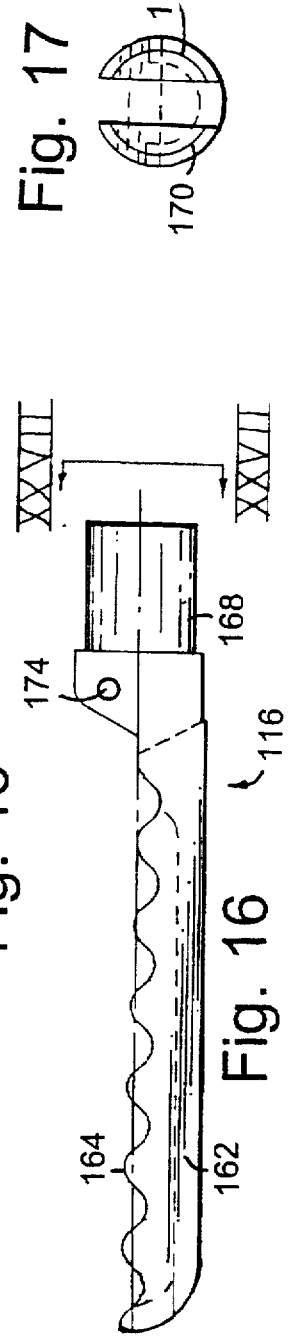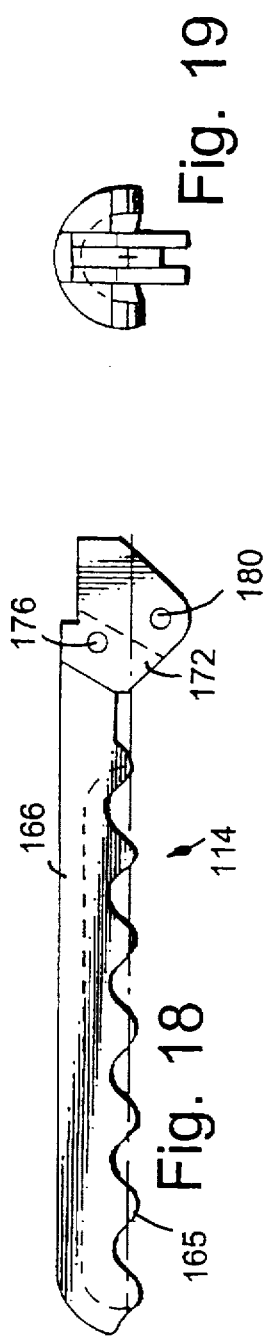

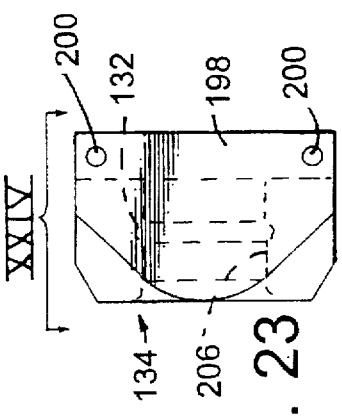
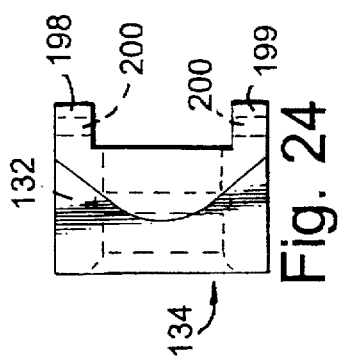
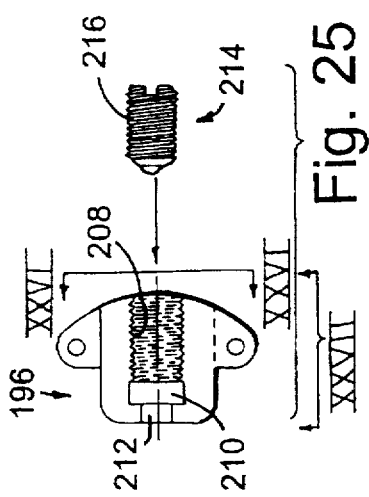
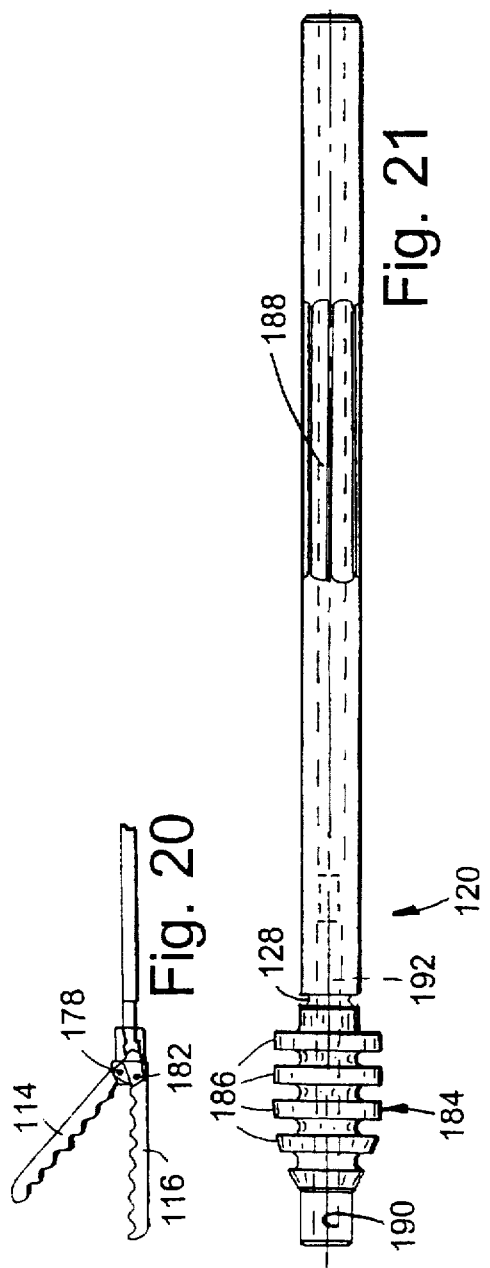
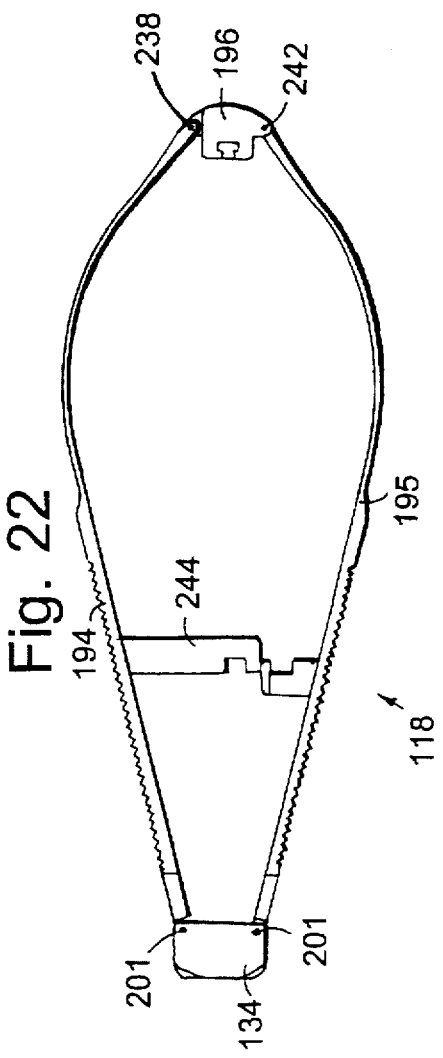

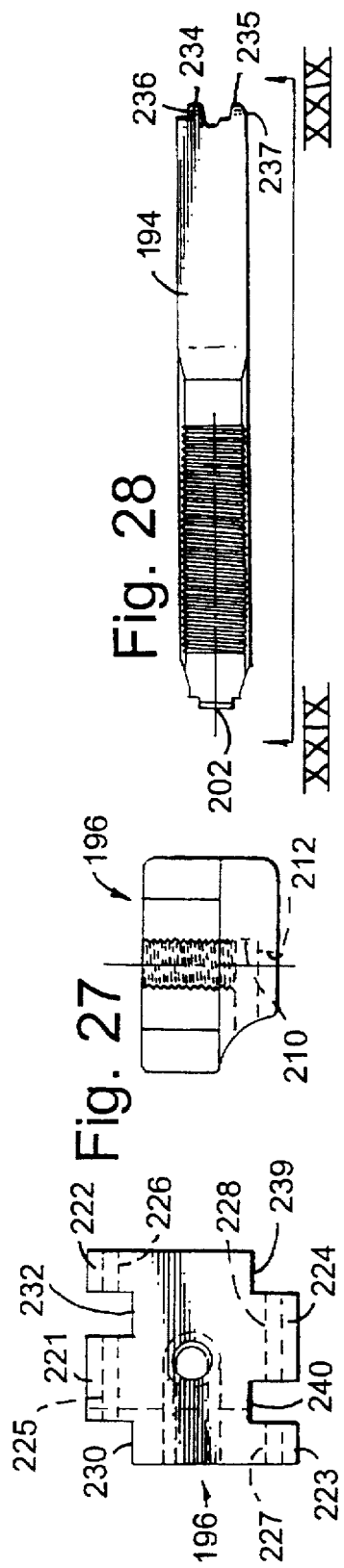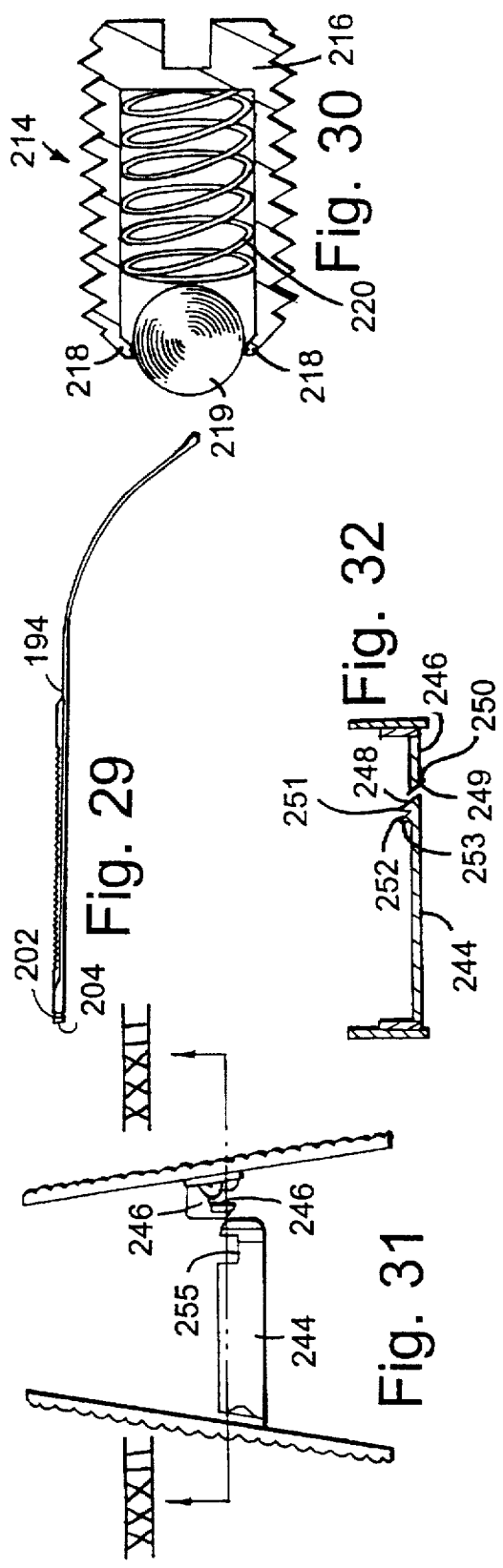

MODULAR ENDOSCOPIC SURGICAL INSTRUMENT

This application claims the benefit of U.S. Provisional application Ser. No. 60/006,602, entitled "MODULAR ENDOSCOPIC SURGICAL INSTRUMENT", filed Nov. 9, 1995.

BACKGROUND OF THE INVENTION

This invention relates generally to surgical instruments for cutting, clamping, holding and shearing functions in surgical operations, and more particularly to modular type surgical instrument systems for microsurgery, laproscopic surgery and endoscopic surgery.

Delicate surgical operations such as microsurgery, laproscopic surgery and endoscopic surgery often require surgical instruments having clamps, scissors, jaws, blades, grippers or other end effectors located at the end of a long, relatively narrow extension rod which provides access to tissue within the body with minimum disturbance of adjacent tissue. Such instruments must provide precise control over the end effectors through the use of control elements at the handle end of the instrument which can be easily and precisely manipulated with the fingers of an operator.

Known instruments for microsurgery, laproscopic surgery and endoscopic surgery have generally comprised an extension rod having an end effector attached at one end of the rod and a handle permanently affixed to the other end of the extension rod. That is, the extension rod and end effector either cannot be removed or cannot be easily removed from the handle. The various components of such instruments are made to very precise tolerances and specifications, and are made in relatively limited quantities. As a result, these instruments and the components thereof are relatively expensive. The useful life of the handle and the end effector are generally very different. Specifically, the end effector generally has a much shorter useful life than the handle. Accordingly, with known microsurgical, laproscopic and endoscopic instruments, the entire instrument is generally discarded when the end effectors are no longer suitable for use, despite the fact that the handle portion of the instrument is still useful and constitutes a significant portion of the cost of the instrument.

Another disadvantage with known microsurgical, laproscopic and endoscopic instruments is that surgeons need to have available numerous expensive instruments of various lengths and having various different types of end effectors for performing various types of surgical functions such as cutting, clamping and holding, even though only a single, or a few, instruments might be needed for a particular surgical procedure. During any particular surgical procedure, a surgeon will generally use only one (or a few) microsurgical, laproscopic or endoscopic instrument at any particular time, although a plurality of different instruments might be needed during the course of the procedure.

SUMMARY OF THE INVENTION

The invention provides a modular type surgical instrument having an extension rod with an end effector at one end thereof, the other end of the extension rod being removably attached to a handle. Thus, a worn end effector can be removed from the handle and replaced with a useable end effector, eliminating economic waste.

The cost associated with having available the various types of instruments which might be needed can be reduced, providing microsurgical, laproscopic and endoscopic instruments which are comprised of interchangeable modular units. A surgical kit or system can be provided comprising one or more handle pieces, each of which can be connected to any of a plurality of extension rods of different lengths and having any of a variety of different end effectors.

BRIEF DESCRIPTION OF THE DRAWING

FIG. 3 is an enlarged top plan view of an end of the actuator rod which is opposite of the end connected to the end effector;

FIG. 5 is an enlarged top plan view of the handle utilized in the instrument shown in FIG. 1, with a portion of the handle being shown in cross-section;

FIG. 6 is a top plan view, in cross-section, of an actuator rod receptacle mounted at the proximal end of the handle shown in FIGS. 1 and 5;

FIG. 7 is a side elavational view, in cross-section, of the receptacle shown in FIG. 6;

FIG. 8 is an end view of the receptacle shown in FIG. 6 and 7, as viewed along lines VIII—VIII of FIG. 6;

FIG. 9 is an exploded top plan view showing the assembly of the actuator rod receptacle with a ball plunger and an electrocautery connector;

FIG. 10 is a side view, in partial cross-section, of the receptacle, ball plunger and electrocautery connector shown in FIG. 9, when fully assembled;

FIG. 11 is a side elevational view of another surgical instrument in accordance with the invention;

FIG. 12 is a side elevational view of the instrument insert which is releasably attachable to the handle portion of the surgical instrument shown in FIG. 11;

FIG. 13 is a fragmentary, side elevational view of the actuation rod used in the instrument shown in FIGS. 11 and 12;

FIG. 14 is an enlarged side elevational view of the distal end of the actuator rod shown in FIG. 13;

FIG. 15 is an enlarged side elevation view of the proximal end of the actuator rod shown in FIG. 13;

FIG. 16 is an enlarged side elevational view of the stationary end effector at the distal end of the instrument shown in FIG. 11;

FIG. 17 is an end view of the stationary end effector shown in FIG. 16, as viewed along lines XVII—XVII of FIG. 16;

FIG. 18 is a side elevational view of the pivotally movable end effector at the distal end of the instrument shown in FIG. 11;

FIG. 19 is an end view of the pivotally movable end effector as viewed along lines XVIV—XVIV of FIG. 18;

FIG. 20 is a fragmentary, side elevation view of the distal end of the actuator rod and end effectors used in the instrument shown in FIG. 11;

FIG. 21 is a side elevational view of the shaft handle adaptor used for connecting the instrument insert of FIG. 12 to the handle portion to form the instrument shown in FIG. 11;

FIG. 22 is a side elevational view of the handle portion of the instrument shown in FIG. 11;

FIG. 23 is a side elevational view of the distal end block of the handle portion shown in FIG. 22;

FIG. 24 is a top plan view of the distal end block shown in FIG. 23;

FIG. 25 is a side elevational view of the proximal end block of the handle portion shown in FIG. 22;

FIG. 26 is an end view of the proximal end block as viewed along lines XXVI—XXVI of FIG. 25;

FIG. 27 is a bottom plan view of the proximal end block as viewed along lines XXVII—XXVII of FIG. 25;

FIG. 28 is a top plan view of the resilient, flexible band of the handle portion shown in FIG. 22;

FIG. 29 is a side elevational view of the resilient, flexible band as viewed along lines XXVIV—XXVIV of FIG. 28;

FIG. 30 is an enlarged elevational cross-section of the ball plunger shown in FIG. 25;

FIG. 31 is a fragmentary, side view of the handle portion shown in FIG. 21; and

FIG. 32 is a cross sectional view along lines XXXII—XXXII of FIG. 31.

DESCRIPTION OF THE PREFERRED EMBODIMENT

Figure 1:
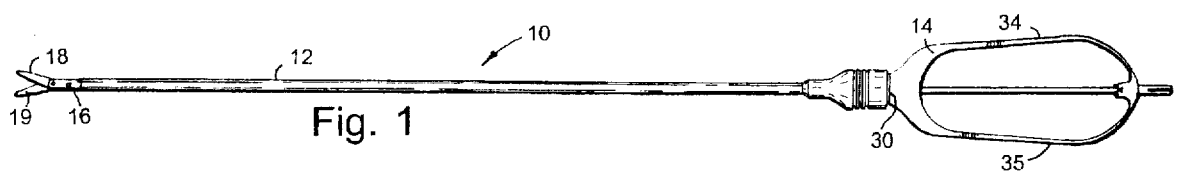
FIG. 1 is a fragmentary, side view of the handle portion shown in FIG. 22, illustrating details of the locking members used for holding the end effector in a closed position.

Referring to the drawings, FIG. 1 shows a surgical instrument 10 including a narrow elongate extension 12 having a handle 14 attached at a proximal end of extension 12 and an end effector 16 attached at a distal end of extension 12. End effector 16 can be any of various clamps, scissors, jaws, blades, grippers, etc., which have opposed members, at least one of which is movable with respect to the other. An infinite variety of end effectors may be used. The illustrated end effector 16 is a scissors type cutting tool having opposed blades 18, 19 which are pivotally mounted on a yoke 20 at the distal end of extension 12.

Figure 2:
FIG. 2 is a top plan view of an actuator rod and end connector utilized in the instrument shown in FIG. 1.

As shown in FIG. 2, extension 12 is comprised of an actuator rod 22 which is slidably retained within yoke 20 for reciprocating movement therein along the longitudinal axis of rod 22. Rod 22 is operatively connected to at least one of the opposed members 18, 19. End effector 16 can be of any suitable design wherein movement of the rod 22 within yoke 20 causes movement and operation of at least one of the opposed members of the end effector to achieve cutting, clamping, holding, shearing or other surgical functions.

As best seen in FIG. 3, the proximal end of actuator rod 22 includes a connector 24 at the end of a small diameter neck portion 26 which extends axially away from the proximal end of the actuator rod. Connector 24 allows quick-connection and disconnection from handle 14 in a manner described herein below.

The actuator rod 22 and end effector 16 are preferably made of stainless steel or other rigid material suitable for surgical use.

Figure 4:
FIG. 4 is a top plan view of a spacer sleeve utilized in the instrument shown in FIG. 1.

A spacer sleeve 28, shown in FIGS. 1 and 4, is a tubular member through which actuator rod 22 passes when instrument 10 is fully assembled for use. Sleeve 28 can be made of stainless steel, aluminum or any of a variety of different types of plastic. A non-conductive plastic or other non-conductive material is preferred if the instrument is to be used in electrosurgery.

Spacer sleeve 28 extends from the base 30 of handle 14 to the proximal end (i.e. the end nearest the handle) of yoke 20 of end effector 16. The primary function of spacer sleeve 28 is to provide an edge surface 32, located at the distal end of the spacer sleeve, which always maintains the end effector at a fixed distance from the base 30 of handle 14 when instrument 10 is fully assembled. When instrument 10 is fully assembled the proximal end of yoke 20 of end effector 16 abuts the distal edge of spacer sleeve 28 so that the distance between base 30 of handle 14 and the proximal end of yoke 20 are fixed during operation of the instrument, as actuator rod 22 is reciprocated within the spacer sleeve and yoke, whereby movement of the actuator rod causes relative movement of the opposed members 18, 19. Spacer sleeve 22 is preferably made of an electrical insulating material such as plastic.

Handle 14 includes opposing actuator members 34, 35, at least one of which is made of a resilient material of suitable thickness so as to provide sufficient flexibility that plastic deformation of the tool does not occur in normal use, and to provide a desired spring rate according to the intended use of the instrument. Compression of one of the actuator members toward the other actuator member causes actuator rod 22 to move with respect to yoke 20 and causes at least one of the opposed members 18, 19 to move with respect to the other. Handle 14 can, for example, be made of a resilient sheet metal such as stainless steel. However, for certain electrosurgical devices, such as electrocautery devices, handle 14 is preferably made of an electrically insulating material such as plastic.

At the proximal end (i.e. the end farthest from the end effector 16) of handle 14, there is provided a receptacle 36 for receiving connector 24 of rod 22. Receptacle 36 (FIGS. 5-8) includes a distal end wall 37 having an open ended slot 38 therein. End wall 37 is spaced from detent 52 by a short base wall 39, leaving a space 40 between end wall 37 and detent 52. Slot 38 is configured to receive neck 26 of rod 22. Connector 24 is larger in lateral diameter than neck 26 such that it extends into space 40 with its distally facing surface 45 engaging the proximally facing surface 44 of end wall 37. Positive engagement between facing surfaces 44 and 45 is preferable maintained by detent 52. Detent 52 comprises a small ball biased in a distal direction by a small spring located in a threaded ball plunger 46, which threads into a threaded receiving socket in receptacle 36. Receptacle 36 together with connector 24 provides quick and easy, snap-type coupling or connection between actuator rod 22 and handle 14.

As shown in FIGS. 9 and 10, receptacle 36 is preferably a cylindrical or barrel shaped member having an axially threaded bore into which ball plunger 46 is threadably received.

Optionally, an electrocautery connector 56 can be threadably received within the threaded bore of receptacle 36. In this case, electrocautery connector 56, ball plunger 46, receptacle 36, and actuator rod 22 are all made of an electrically conductive material and provide a continuous electrical connection between connector 56 and end effector 16.

In operation, compression of the normally outwardly bowed actuating members 34, 35 toward each other causes the proximal movement of actuator rod 22 with respect to spacer sleeve 28 and yoke 20. The movement of linkage rod 22 is guided slidingly within the hollow portion of tubular spacer sleeve 28. The proximal movement of rod 22 effects the proximal movement of opposed members 18, 19.

Release of actuating member 34, 35 causes the resiliently flexible actuating members to return to their original position. This return to the original position causes the distal movement of linkage rod 22 with respect to tubular spacer sleeve 28 and the return of opposed members 18, 19 back to the open position.

A second embodiment of the invention is shown in FIGS. 11–32. With reference to FIG. 11, a surgical instrument 110 generally includes an instrument insert 112 including end effectors 114, 116, and a handle portion 118. Instrument insert 112 (shown in FIG. 12) is detachably connected to handle portion 118 by means of a quick-connecting, snap-together type connection. With reference to FIG. 12, the instrument insert 112 includes a shaft handle adaptor 120 having an grip portion 184 and a tubular extension 124, a tubular 126, and an actuator rod 127 adapted to be connected at its proximal end to the proximal end of handle portion 118 and connected at its distal end to pivotally movable end effector 114. Shaft handle adapter 12 includes a circumferential groove 128 (FIG. 21) in which an elastic O-ring 130 is received. Groove 128 and O-ring 130 are proximally spaced from the distal end of grip portion 184 so that O-ring 130 engages an internal circumferential groove 132 (FIGS. 23 and 24) in distal end block 134 when instrument insert 112 is fully inserted into handle portion 118. Engagement between the elastic O-ring 130 and internal circumferential groove 132 of distal end block 134 facilitates quick, snap-together connection between the instrument insert 112 and the handle portion 118. Actuator rod 127 is comprised of a proximal rod portion 136 (FIG. 13) connected at its distal end to a distal rod portion 138. Distal rod portion 138 is connected to proximal rod portion 136 by inserting the proximal end of distal rod portion 138 into a cylindrical bore 140 at the distal end of proximal rod 136, and brazing the distal rod portion 138 to the proximal rod portion 136. Distal rod portion 138 has a smaller diameter than proximal rod portion 136, the diameter of the distal rod portion being approximately equal to the diameter of cylindrical bore 140. Intermediate between the distal and proximal ends of the proximal rod portion 136 is a short narrow diameter section 142 defining opposing stop walls 144, 145 which are engaged by a stop pin 146 (FIG. 12) which projects radially through tubular extension 124 of insert 112 into the space defined between the stop walls 144, 145 to limit axial displacement of actuator rod 127 with respect to the shaft handle adaptor 120 and tubular body or cannula 126, and thereby limits the pivotal motion of end effector 114 with respect to stationary end effector 116. At the proximal end of proximal rod portion 136 there is provided a connector 148 having a larger diameter cylindrical portion 150 connected to the proximal end of proximal rod portion 136 by a reduced diameter neck portion 152 (FIG. 15). The proximal end of connector 148 includes a dimple or recess 154 which is configured to serve as a seat for latch member 156 (FIG. 28), which is resiliently urged against the proximal end of connector 148 to lock or retain the instrument insert 112 in place on handle portion 118. As shown in FIG. 14, the distal end of distal rod portion 138 includes a pivot arm 158 defining a pivot aperture 160. Pivot arm 158 extends from the distal end of distal rod portion 138 at an angle so that the pivot aperture 160 is spaced from the longitudinal axis of actuator rod 127. Instrument insert 112 includes thoothed tissue forcep end effectors, including a stationary end effector 116 (FIG. 16) which is fixedly connected to the distal end of cannula 126, and a pivotally movable end effector 114 (FIG. 18) which is pivotally connected to stationary end effector 116. Stationary end effector 116 includes a forcep arm 162 having undulating or thoothed edges 164 which face complementary thoothed edges 165 on forcep arm 166 of movable end effector 114. The teeth or undulations of thoothed edges 164 and 165 are configured so that the teeth will intermesh with the peaks of the teeth or undulations of thoothed edges 164 generally disposed within the valleys of the teeth or undulations of thoothed edges 165 when movable end effector 114 is pivoted into engagement with the stationary end effector 116. The undulations or teeth facilitate gripping of tissue. Stationary end effector 116 includes a pair of spaced apart proximally extending connectors 168 having curved outer walls 170 which are configured to engage the interior walls at the distal end of cannula 126. Connectors 168 serve to properly align and fit the stationary end effector 116 to the distal end of cannula 126, so that end effector 116 can be subsequently brazed to cannula 126. The proximal end of pivotally movable end effector 114 includes a proximally extending pivot arm 172 which is configured to be inserted into the space between connectors 168. A pivot aperture 174 through the proximal end of stationary end effector 116 is aligned with a pivot aperture 176 through the proximal end of pivotally movable end effector 114, and a pivot pin 178 is inserted through the aligned apertures 174 and 176 as shown in FIG. 20 to pivotally connect end effector 114 to stationary end effector 116. Pivot arm 172 includes a second aperture 180 which is aligned with pivot aperture 160 of pivot arm 158 at the distal end of actuator rod 127, and a pivot pin 182 (FIG. 20) is extended through aligned apertures 180 and 160 to pivotally connect the proximal end of pivotally movable end effector 114 to the distal end of actuator rod 127, so that when actuator rod 127 is moved axially in the proximal direction with respect to cannula 126, end effector 114 is rotated from the opened position shown in FIG. 20 to a closed position wherein the surfaces 164 and 165 of forcep arms 162 and 166 are urged together. The end effectors 114 and 116, pivot pins 178 and 182, cannula 126, and actuator rod portions 136 and 138 are preferably made of stainless steel, but can be comprised of other materials which are suitable for surgical use. When materials other that stainless steel are used, the various brazed connections can be replaced with other appropriate connections. For example, if surgically acceptable, plastic materials are used, the fixed connection between the proximal rod portion 136 and distal rod portion 138, and between the stationary end effector 116 and the distal end of the cannula 126 can be a frictional-fit connection, an adhesive connection, a thermal fusion connection, or other appropriate connection. Further, it is conceivable that certain connections may be eliminated by forming two or more of the parts as a single unit.

In FIG. 21, there is shown a shaft handle adaptor 120. A grip portion 184 is provided near the distal end of shaft handle adaptor 120. The grip portion 184 includes a plurality of axially spaced apart rings or flanges 186 which project radially outwardly from the outer walls of the tubular adaptor portion to form a plurality of concentric alternating ridges and grooves which facilitate gripping of the shaft handle adaptor 120, allowing easy removal of the insert 112 from the handle portion 118. Spaced a short distance proximally of the grip portion 184 is a groove 128 for receiving an elastic O-ring 130 (see FIG. 12) which engages a corresponding internal circumferential groove in a bore through the distal end block 134 of handle portion 118. Located intermediate between the opposing ends of the shaft handle adaptor 120 is a flatted section 188 having a polygonal transverse cross sectional shape to facilitate gripping of the tubular extension 124 of shaft handle adaptor 120, so that the shaft handle adaptor can be easily rotated as desired to properly arrange the end effectors 114 and 116 with respect to tissue which is to be gripped by the forceps, without having to rotate the entire instrument, including the grip portion 118. This allows a surgeon to properly arrange the forceps or end effectors 114, 116 without having to rotate his/her wrist into an uncomfortable or awkward position. The proximal end of the cannula 126 is rigidly connected to the distal end of the shaft handle adaptor 120 by means of a press-fit engagement between the outer circumferential wall of the cannula 126 and the inner circumferential wall 190 of an axial throughbore 192 which extends through from one end to the other end of the shaft adaptor 120. Other means can be employed for connecting the cannula 126 to the shaft handle adaptor 120, although the frictional engagement between the outer wall of the cannula 126 and the inner wall 190 of the axial throughbore 192 has been found to be adequate to firmly hold shaft handle adaptor 120 and cannula 126 together and to prevent either axial or rotational movement of the cannula with respect to the shaft handle adaptor during normal use of the instrument 110. The desired press-fit or frictional engagement between the shaft handle adaptor 120 and the cannula 126 can be achieved by providing a cannula having a diameter which is slightly larger than the diameter of the axial throughbore 192. Appropriate dimensions for achieving a suitable frictional engagement or press-fit between the shaft handle adaptor 120 and the cannula 126 can be easily determined by those having ordinary skill in the art.

The handle portion 118 is shown in greater detail in FIG. 22. Handle portion 118 is generally comprised of a pair of resilient, flexible bands 194 and 195, each of which is connected at opposite ends thereof to distal end block 134 and proximal end block 196 to form a continuous loop having opposing ends and opposing outwardly biased bands 194 and 195. Distal end block 134 is shown in greater detail in FIGS. 23 and 24. Distal end block 134 includes a pair of proximally extending, spaced apart flanges 198, 199. Flanges 198 and 199 each include a pair of pivot apertures 200 located at opposite ends of flanges 198 and 199. Each of the pivot apertures on flange 198 is aligned with a pivot aperture on flange 199 as shown in FIG. 24. As shown in FIGS. 28 and 29, band 194 includes a distally extending portion 202 having a throughbore 204. Distally extending portion 202 is configured to fit in the space between opposing flanges 198 and 199 with throughbore 204 aligned with the aligned pivot apertures 200 on flanges 198 and 199. The distal end of band 194 is connected to distal end block 134 by inserting a pivot pin 201 through the aligned apertures 200 in the flanges 198 and 199, and through the aligned throughbore 204 at the distal end of flexible band 194. Flexible band 195 is substantially a mirror image of flexible band 194 and is connected at the pivot apertures 200 on the opposing side of the distal end block in a generally similar manner. Distal end block 134 includes a throughbore 206 through which shaft handle adaptor 120 extends when instrument insert 112 is attached to handle portion 118 as shown in FIG. 1. Throughbore 206 includes a circumferential groove 132 for receiving elastic O-ring 130. When instrument insert 112 is inserted into the handle portion 118, the engagement between the elastic O-ring 130 and the internal circumferential groove 132 in throughbore 206 provides an easily perceptible tactile indication that the adaptor portion has been properly located and snap-fitted to the handle portion 118. Details of the proximal end block 196 are shown in FIGS. 25–27. Proximal end block 196 includes a threaded bore 208 which is axially aligned with the actuator rod 127, cannula 126 and shaft handle adaptor 120 when the instrument 110 is assembled as shown in FIG. 1. Threaded bore 208 extends from a proximal end of the proximal end block 196 to a recess 210 which is configured for receiving the larger diameter cylindrical portion 150 of connector 148 at the proximal end of actuator rod 127. Adjacent recess 210 is a shallower recess 212 which is configured to receive the neck portion 152 of connector 148. Adjacent recesses 210 and 212 together act as a fitted receptacle having surfaces abutting surfaces on connector 148 to prevent axial movement of actuator rod 127 with respect to proximal end block 196. That is, connector 148 and recesses 210 and 212 are cooperatively configured to facilitate attachment of the proximal end of actuator rod 127 to proximal end block 196. A ball plunger 214 (FIGS. 25 and 30) is generally comprised of an externally threaded, hollow cylindrical body 216 having a bezel 218 which retains a ball 219 which is urged in the distal direction by a tensioned spring 220 housed within the hollow portion of the cylindrical body 216. When instrument insert 112 is connected to handle portion 118, the proximal end of connector 148 engages ball 219 causing the ball to be depressed proximally against the resistance of spring 220 until the ball becomes seated in dimple or recess 154. Ball 219 urged against and seated in recess 154 provides a snap lock engagement between connector 148 and proximal end block 196 to prevent actuator rod 127 from becoming detached from proximal end block 196 during normal use of the surgical instrument. However, the force exerted upon ball 219 by spring 220 is sufficiently low so that connector 148 can be snap disconnected from the receptacle in proximal end block 196, defined by recesses 210 and 212, without undue effort when it is desired to disconnect instrument insert 112 from handle portion 118. Proximal end block 196 includes a plurality of laterally extending ears 221, 222, 223 and 224 which project from opposite sides of the proximal end block 196. Ears 221 and 222 each include a throughbore 225 and 226, respectively which are axially aligned with each other. Likewise, ears 223 and 224 include throughbores 227 and 228 respectively which are also axially aligned. Ear 221 is off-set from one of the side edges of proximal end block 196 to define a corner notch 230 in block 196, and ear 222 is spaced from ear 221 to define a lateral notch 232 therebetween. The proximal end of flexible band 194 includes a pair of proximally extending spaced apart connector ears 234 and 235 having axially aligned throughbores 236 and 237. Ears 234 and 235 are disposed in the corner notch 230 and lateral notch 232, respectively, with the throughbores 236 and 237 axially aligned with throughbores 225 and 226 of ears 221 and 222. A pivot pin 238 (FIG. 22) extends through throughbores 225, 226, 236 and 237 to pivotally connect flexible band 194 to one side of proximal end block 196. Likewise, flexible band 195 includes a pair of spaced apart connecting ears similar to ears 234 and 235 and having throughbores similar to throughbores 236 and 237, with the connector ears of flexible band 195 being located at notches 239 and 240 adjacent one side of ear 224 and between ears 223 and 224, respectively. The proximal end of flexible band 195 is connected to proximal end block 196, on the side opposite the side at which flexible band 194 is connected, with a pivot pin 242 in a manner similar to the manner in which flexible band 194 is connected to proximal end block 196. Handle portion 118 includes a locking device for holding end effectors 114 and 116 in a closed position. The locking device includes a first locking member 244 (FIGS. 31 and 32) extending from flexible band 194 toward flexible band 195, and a second locking member 246 projecting from flexible band 195 toward flexible 194. The locking members are shown in the disengaged or unlocked position. In order to engage the locking members 244 and 246, to hold end effectors 114 and 116 in the closed position, flexible bands 194 and 195 are urged toward each other so that parallel camming surfaces 248 and 249 on locking members 244 and 246 come into contact with each other. As the locking members are urged together, locking member 244 is deflected downwardly and locking member 246 is deflected upwardly with respect to the orientation shown in FIG. 32. As the camming surfaces are urged together, camming surfaces 248 and 249 slide in opposite directions until ridge 250 of locking member 246 slides over ridge 251 of locking member 244, at which time the resilient locking members 244 and 246 spring back upwardly and back downwardly, respectively, with the ridge 250 of locking member 246 becoming wedged between ridges 251 and 252 of locking member 244. In order to disengage or unlock the locking members 244 and 246, flexible bands 194 and 195 are further urged together to cause camming surface 249 of locking member 244 to slide upwardly against camming surface 252 of locking member 244 and over ridge 253. Beyond ridge 253 of locking member 244, a notch 255 (FIG. 31) is defined. Similarly, a notch 256 is provided on locking member 246. As the ridge 250 of locking member 246 slides past the ridge 254 of locking member 244, the ridges become disposed between the respective notches to allow disengagement of the locking device.

Instrument insert 112 can be prepared by first brazing the proximal rod portion 136 and distal rod portion 138 together as described above. Thereafter, the stationary end effector 114 can be brazed to the end of the cannula 126, as described above. The proximal end of the cannula 126 can then be press-fit into the distal end of the shaft handle adaptor 120, as previously described. The distal end of the assembled actuator rod 127 can then be inserted through the proximal end of the shaft handle adaptor 120, through the cannula 126, and past the stationary end effector 116, so that pivot arm 158 and pivot aperture 160 are accessible. Thereafter, the pivotally movable end effector 114 can be pinned to the end of the actuator rod, as described above. The pivotally moveable end effector 116 then is properly positioned on the end of cannula 126 and pinned in place, as described above. As the pivotally movable end effector 114 is properly positioned on the cannula 126, the attached actuator rod is slid back into the cannula 126. The instrument insert 112 can be finished by inserting stop pin 146 through shaft handle adaptor 120 so that it projects into the space between stop walls 144 and 145 of the narrow diameter section 142. Elastic O-ring 130 can generally be positioned in groove 128 at generally any time during the assembly process.

Handle portion 118 is assembled by pinning the opposing ends of the resilient, flexible bands 194 and 195 to the distal end block 134 and proximal end block 196 to form a continuous loop type flexible handle. Locking member 244 and 246 can optionally be riveted or otherwise attached to flexible bands 194 and 195 using rivets or other suitable fasteners.

The various components of the handle portion 118, including the distal end block 134, the proximal end block 196, and the opposing flexible bands 194 and 195, as well as the pins connecting the bands to the blocks, are preferably formed of stainless steel, but other suitable materials can be used if desired. Likewise, the optional locking members 244 and 246 are preferably made of stainless steel.

The shaft handle adaptor 120 is preferably made of an engineered thermoplastic, such as ULTEM® 1000, which is an engineered plastic material based on polyetherimide resins, and sold by the General Electric Co., Polymers Product Department.

The instrument insert 112 is attached to the handle portion 118 by inserting the proximal end of instrument insert 112 through throughbore 206 of distal end block 134. Instrument insert 112 is urged through throughbore 206 of distal end block 134 until elastic O-ring 130 engages the internal circumferential groove 132 of distal end block 134. Thereafter, the larger diameter cylindrical portion 150 of connector 148 is inserted down into recess 110 until dimple or recess 154 is engaged by the spring biased ball 219 of ball plunger 214, causing the proximal end of instrument insert 112 to be retained by proximal end block 196 with sufficient force so that the instrument insert 112 does not become disengaged from the end block 196 during normal use of the surgical instrument 110. Disconnection of the instrument insert 112 is achieved by merely reversing the attachment procedure set forth above. More specifically, the larger diameter cylindrical portion 150 of connector 148 is removed from recess 210, and then the insert 112 is separated from the handle portion 118 by grasping grip portion 184 and handle portion 118 and pulling the insert from the handle portion.

Handle portion 118 can be used with a variety of different sized, and different types of instrument inserts which are generally similar to instrument insert 112. More specifically, instrument inserts having various types of end effectors, such as scissors or forceps, can be utilized interchangeably with the handle portion 118. Further, instrument inserts having different size cannulas 126 and different size end effectors can be used interchangeably with handle portion 118. In particular, the instrument inserts which can be interchangeably used with handle portion 118 can have, for example, any of the commonly used cannula diameters, such as 2 millimeters, 3 millimeters, 4 millimeters or 5 millimeters.

While the foregoing describes use of the instrument in the field of surgery, the instrument may find appropriate uses in other applications requiring a small, simple tool. It should be understood that end effector 16 comprised of opposed blades 18, 19, are just an example and that various cutting blades, saw blades, needle holders, scissors, tissue forceps, smooth holding platforms, etc., could be substituted.

Of course, it is understood that the foregoing describes the preferred embodiment of the invention, and that various changes and alterations can be made without departing from the spirit and broader aspects of the invention as set forth in the appended claims.

The embodiments of the invention in which an exclusive property or privilege is claimed are defined as follows:

1. A surgical instrument comprising:
a handle;
an end effector;
an elongate tubular sleeve extending between and opposing said end effector and said handle;
a reciprocating actuator rod disposed within said sleeve;
said end effector operably connected to a distal end of said actuator rod, said end effector having opposed members, at least one of which is movable with respect to another upon sliding movement of said actuator rod within said sleeve;
said handle including a pair of opposed actuating members, at least one of which is resiliently flexible, said handle having a first end connected to a proximal end of said tubular sleeve, and a second end releasably snap connected to a proximal end of said actuator rod, whereby compression of said flexible actuating member toward the other actuating member causes said actuator rod to move at least one of said opposed members of said end effector with respect to another of said opposed members of said end effector.

2. The surgical instrument of claim 1, wherein said actuator rod is releasably connected to said handle by means of a connector at the proximal end of said actuator rod which is received within a receptacle located at the proximal end of said handle, said receptacle releasably retaining said connector, whereby a quick and easy snap-type connection is achieved between said actuator rod and said handle.

3. The surgical instrument of claim 2, wherein said connector is cylindrical and is at the end of a small diameter neck portion which extends axially away from the proximal end of said actuator rod.

4. The surgical instrument of claim 3, wherein said receptacle further comprises a ball plunger having a distally facing hemispherical surface which engages a proximally facing surface of said connector.

5. The surgical instrument of claim 4, wherein said ball plunger is comprised of a member having a ball which is urged distally by a spring contained within said ball plunger.

6. The surgical instrument of claim 5, wherein said receptacle is a cylindrical member having an axially threaded bore into which said ball plunger is threadably received.

7. A surgical instrument comprising:

a handle;

an end effector;

an elongate tubular sleeve extending between and opposing said end effector and said handle;

a reciprocating actuator rod disposed within said sleeve;

said end effector operably connected to a distal end of said actuator rod, said end effector having opposed members, at least one of which is movable with respect to another upon sliding movement of said actuator rod within said sleeve; said handle including a pair of opposed actuating members, at least one of which is resiliently flexible, said handle having a first end connected to a proximal end of said tubular sleeve, and a second end releasably connected to a proximal end of said actuator rod, whereby compression of said flexible actuating member toward the other actuating member causes said actuator rod to move at least one of said opposed members of said end effector with respect to another of said opposed members of said end effector;

wherein said actuator rod is releasably connected to said handle by means of a connector at the proximal end of said actuator rod which is received within a receptacle located at the proximal end of said handle, said receptacle releasably retaining said connector, whereby a quick and easy snap-type connection is achieved between said actuator rod and said handle;

wherein said connector is cylindrical and is at the end of a small diameter neck portion which extends axially away from the proximal end of said actuator rod;

wherein said receptacle further comprises a ball plunger having a distally facing hemispherical surface which engages a proximally facing surface of said connector wherein said ball plunger is comprised of a member having a ball which is urged distally by a spring contained within said ball plunger;

wherein said receptacle is a cylindrical member having an axially threaded bore into which said ball plunger is threadably received; and an electrocautery connector which is threadably received within the threaded bore of said receptacle.

8. The surgical instrument of claim 7, wherein said electrocautery connector, said ball plunger, said receptacle, and said actuator rod are all made of an electrically conductive material and provide a continuous electrical connection between said electrocautery connector and said end effector.

9. A surgical instrument comprising:

a handle;

an end effector;

an elongate tubular sleeve extending between and opposing said end effector and said handle;

a reciprocating actuator rod disposed within said sleeve;

said end effector operably connected to a distal end of said actuator rod, said end effector having opposed members, at least one of which is movable with respect to another upon sliding movement of said actuator rod within said sleeve;

said handle including a pair of opposed actuating members, at least one of which is resiliently flexible, said handle having a first end connected to a proximal end of said tubular sleeve, and a second end releasably connected to a proximal end of said actuator rod, whereby compression of said flexible actuating member toward the other actuating member causes said actuator rod to move at least one of said opposed members of said end effector with respect to another of said opposed members of said end effector;

wherein said actuator rod is releasably connected to said handle by means of a connector at the proximal end of said actuator rod which is received within a receptacle located at the proximal end of said handle, said receptacle releasably retaining said connector, whereby a quick and easy snap-type connection is achieved between said actuator rod and said handle;

wherein said connector is cylindrical and is at the end of a small diameter neck portion which extends axially away from the proximal end of said actuator rod; and an electrocautery connector which is threadably received within the threaded bore of said receptacle.

10. The surgical instrument of claim 9, wherein said electrocautery connector, said ball plunger, said receptacle, and said actuator rod are all made of an electrically conductive material and provide a continuous electrical connection between said electrocautery connector and said end effector.

11. A surgical instrument comprising:

a handle;

an end effector;

an elongate tubular sleeve extending between and opposing said end effector and said handle;

a reciprocating actuator rod disposed within said sleeve;

said end effector operably connected to a distal end of said actuator rod, said end effector having opposed members, at least one of which is movable with respect to another upon sliding movement of said actuator rod within said sleeve;

said handle including a pair of opposed actuating members, each of which is a resiliently flexible band having gripping surfaces, said handle having a first end connected to a proximal end of said tubular sleeve, and a second end releasably connected to a proximal end of said actuator rod, whereby compression of said flexible actuating member toward the other actuating member causes said actuator rod to move at least one of said opposed members of said end effector with respect to another of said opposed members of said end effector.

* * * * *

UNITED STATES PATENT AND TRADEMARK OFFICE
CERTIFICATE OF CORRECTION

Page 1 of 2

PATENT NO. : 5,752,972
DATED : May 19, 1988
INVENTOR(S) : Thomas J. Hoogeboom

It is certified that error appears in the above-identified patent and that said Letters Patent is hereby corrected as shown below:

*Column 2, line 6;
   "DRAWING" should be --DRAWINGS--.

*Column 2, line 26;
   "elavational" should be --elevational--.

*Column 2, lines 47 & 61;
   "elevation" should be --elevational--.

*Column 4, line 39;
   "preferable" should be --preferably--.

*Column 5, line 59;
   "thoothed" should be --toothed--.

*Column 5, lines 65 and 66;
   "thoothed" should be --toothed--.

*Column 6, lines 1, 3 & 4;
   "thoothed" should be --toothed--.

UNITED STATES PATENT AND TRADEMARK OFFICE
CERTIFICATE OF CORRECTION

PATENT NO. : 5,752,972
DATED : May 19, 1988
INVENTOR(S) : Thomas J. Hoogeboom

It is certified that error appears in the above-identified patent and that said Letters Patent is hereby corrected as shown below:

*Column 6, line 37;
  "that" should be --then--.

*Column 8, line 7;
  "Delete "surfaces" (1st occurrence).

*Column 8, lines 65;
  Before "194", insert the word --band--.

*Column 9, line 52;
  "member" should be --members--.

Signed and Sealed this

Third Day of November, 1998

BRUCE LEHMAN

*Attest:*

*Attesting Officer*  *Commissioner of Patents and Trademarks*